United States Patent [19]

Backman et al.

[11] Patent Number: 4,743,546

[45] Date of Patent: May 10, 1988

[54] CONTROLLED GENE EXCISION

[75] Inventors: Keith C. Backman, Bedford; Ramaswamy Balakrishnan, Framingham, both of Mass.

[73] Assignees: Biotechnica International, Inc., Cambridge, Mass.; H. J. Heinz Company, Pittsburgh, Pa.

[21] Appl. No.: 701,091

[22] Filed: Feb. 13, 1985

[51] Int. Cl.[4] .................. C12P 13/22; C12P 21/00; C12P 21/02; C12N 15/00; C12N 1/20; C12N 7/00

[52] U.S. Cl. .................. 435/108; 435/68; 435/70; 435/172.3; 435/253; 435/320; 435/849; 935/14; 935/42; 935/43

[58] Field of Search ............ 435/68, 70, 172.1, 172.3, 435/317, 108; 536/27

[56] References Cited

PUBLICATIONS

Howard et al., in *Experimental Manipulation of Gene Expression*, Academic Press, 1983, pp. 137–153.
Murray et al., in *Lambda II*, Cold Spring Harbor Press, 1983, pp. 395–432.
Leplatois et al., (1983), Biochimie, 65:317–324.
Wilson et al., (1979), J. Mol. Biol., 132:471–491.
Murray et al., (1979), J. Mol. Biol., 132:493–505.
Struhl, (1981), J. Mol. Biol., 152:517–533.
Plasterk, (1983), Virol., 127:24–36.
Echols et al., "Control of Integration and Excision", *Lambda II*, (Hendrix et al., Ed.), CSH Laboratory, (1983), pp. 75–92.
Joyce et al., (1984), J. Bacteriol., 158:636–643.

*Primary Examiner*—Thomas G. Wiseman
*Assistant Examiner*—Thomas D. Mays

[57] ABSTRACT

An *Escherichia coli* chromosomal DNA segment is engineered for controllable excision and loss from the *E. coli* cell population. The DNA segment has a gene determining a function that is lost in the absence of that chromosomal segment. Specifically, the segment includes a pair of lambdoid phage att sites positioned at opposite ends thereof, and a gene encoding the function. The *E. coli* cell includes DNA encoding lambdoid phage int and xis, positioned for transcription under control of an external stimulus. By excising the chromosomal DNA segment once a desired cell population is achieved, cell growth and diversion of intermediates from a desired fermentation product are diminished or avoided.

30 Claims, 8 Drawing Sheets

FIG. 1

FIG. 2
pKB720

FIG. 3
pBR322

FIG. 4
pKB742

FIG. 5
pKB757

FIG. 6
pKB760

FIG. 7
pKB767

FIG. 8
pKB788

FIG. 9
pKB791

FIG. 10
pKB800

FIG. II
pKB803

FIG. 12
xKB803

FIG. 13

FIG. 14
pKB712

FIG. 15
pKB750

FIG. 16

CONTROLLED GENE EXCISION

BACKGROUND OF THE INVENTION

This invention relates to controlled cessation of a particular cell function.

One instance in which controlled cessation of a cell function is useful involves microbial fermentation of a desired product. To achieve a desired microbial cell population, the cells are allowed to undergo an exponential ("log") phase of cell growth. When a suitable cell population density is reached, it may be advantageous to halt cell-growth so that cellular resources and metabolic energy are not diverted from the production of the desired compound. Ideally, a mechanism to achieve this goal should be absolute, so that some cells in the population will not circumvent the growth control and overgrow the culture.

One way to control cell growth is by limiting the availability of one or more nutrients that the cell requires for growth. Once the limited amount of a nutrient is used, cell growth ceases. Cells may be mutated or engineered so that they require a nutrient in order to grow. For example, if the nutrient is a particular amino acid such as tyrosine, cells are mutated or engineered to create a defect in the cell's natural pathway for synthesizing that amino acid. The cells then may be provided the amino acid in an amount selected to allow them to achieve a desired cell population; when the cells reach that population, they become starved for the amino acid and cannot grow.

SUMMARY OF THE INVENTION

The invention features, generally, integrating a gene in a bacterial chromosome and controlling excision of the gene from the chromosome in response to an external stimulus, so that the gene is lost from the cell. Such integration and excision are accomplished using DNA comprising:

(a) a vector that is incapable of replicating autonomously in the host and that includes the gene (or a site for the insertion of the gene) and an attachment site corresponding to an attachment site on the host chromosome [As used in this application, attachment site means a site which corresponds to an attachment site on the bacterial chromosome and which serves as a substrate for enzymes catalyzing site-specific recombination to produce integration in and excision from the chromosome.];

(b) DNA capable of causing the integration of vector (a) in the bacterial chromosome and DNA capable of causing the excision of that vector therefrom; and (c) DNA capable of effecting control of excision of vector (a) from the bacterial chromosome in response to an external stimulus.

In preferred embodiments, the DNA is used to transform host cells that are to synthesize a desired compound. The gene to be integrated and controllable excised codes for a cell-growth function that reduces the yield of the desired compound either by converting the desired compound into other compounds or by shunting intermediates away from the desired compound's biosynthetic pathway. Thus, the gene is integrated in the host cells to improve growth, and then it is excised and lost from the cells to improve compound production. For phenylalanine production, the gene on the excision vector preferably is one or more of tyrA, tyrR or trpE. For tryptophan production, the gene preferably is tna (tryptophanase), trpR, aroP, tyrA or pheA. For proline production, the gene preferably is one coding for proline oxidase. For threonine production, the gene preferably is one coding for an enzyme in the isoleucine biosynthesis pathway. The ppc (phosphoenolpyruvate carboxylase) gene is essential for growth in some strains and provides suitable growth control for producing desired compounds generally. The host bacterial genome lacks the ability, in the absence of the gene of interest, to produce enough of that gene's product to sustain growth. Most preferably, the gene of interest is entirely missing from the host genome, either naturally or by design, and the host genome lacks sufficient homology with any portion of the vector to permit vector integration in the absence of (b). Also in preferred embodiments, the DNA of the vector includes elements (b) and (c) above, and the vector contains DNA encoding an attachment site (att) derived from an attachment site of a naturally occurring bacteriophage, such a phage lambda or a lambdoid phage. As used in this application, DNA "derived from a particular DNA segment" such as an att site means DNA segments that are identical to that particular DNA segment or that are natural, synthetic, or engineered variations of the DNA segment which conserve the specified or desired function. The DNA encoding integration and excision functions is derived from a naturally occurring bacteriophage. The means for controlling excision of the vector is a promoter regulating transcription of an excision enzyme gene, together with a gene that codes for repressor for that promoter, the repressor being subject to external control such as the lambda cI gene product which loses its repression function at elevated temperatures. The DNA capable of causing vector integration or excision also can be provided by a helper phage, which is itself incapable of integration in the host chromosome.

The invention is particularly useful where the organism synthsizes the desired compound from a precursor that also appears on a synthetic pathway that is essential for cell growth. In such organisms, an enzyme catalyzing a biochemical reaction occurring after one of these common precursors could shunt the precursors toward cell growth and away from production of the desired compound. The cell growth pathway is enabled by allowing expression of the enzyme that shunts the precursor into the growth pathway during the log growth phase. By disenabling the expression of genetic material encoding the enzyme for the cell-growth pathway after a suitable cell population density has been reached, the common precursor will be channeled into the synthesis of the desired compound, and cell growth will cease due to the removal of an essential enzyme.

If a small number of cells continue to express the genetic material necessary for growth, they might overgrow their disenabled siblings and reduce the product yield. This problem is avoided because, once deleted from the bacterial chromosome, the genetic material coding for the growth function is unable to replicate autonomously. The gene eventually will "dilute out" as the cells continue to divide, and it will be lost from the cells completely. Since regions on the vector that are substantially homologous with the DNA of the host chromosome are avoided, the probability of the vector reintgrating in the host chromosome through a homologous recombination event is extremely low. Thus, integration can only occur by site specific recombination at the desired att site, and the ability to grow and divert important product precursors into cell growth can be disenabled reliably as desired to enhance production of the desired compound.

Other features and advantages of the invention will be apparent from the following description of the preferred embodiments and from the claims.

DESCRIPTION OF THE PREFERRED EMBODIMENTS

We first describe the drawings.

Drawings

Structure

The preferred embodiment described below relates to one specific system useful in microbial production of phenylalanine. Specifically, the system enables controlled expression of the tyrA gene, a critical gene in the tyrosine biosynthesis pathway. Since tyrosine is relatively insoluble, it is difficult to prepare stock solutions suitable for supplementing a medium used for growing tyrosine auxotrophs. Therefore, tyrosine prototrophy in cells to be used for compound producton is a desirable trait for fast growth and efficient culture when log phase growth of the culture is required. However, the tyrosine biosynthesis pathway shares many common metabolic precursors and enzymatic steps with the phenylalanine synthesis pathway, and it is useful to use tyrA$^-$ organisms to make phenylalanine because such organisms do not siphon away phenylalanine pathway intermediates and thereby reduce the phenylalanine yield and additionally because tyrA$^-$ cells quickly become starved for tyrosine and induce the synthesis of tyrosine precursors which then are used for phenylalanine synthesis.

The preferred embodiment described below is only one example of the use of the invention to provide controlled expression of cell-growth functions which may be detrimental once the desired cell population has been achieved and compound production has begun. Those skilled in the art will recognize that there are a great number of possible cell-growth functions that can be controlled using the invention to enhance production of a desired compound.

The excision vector comprises DNA from a lysogenic bacteriophage lambda, such as cI$_{857}$S$_7$, which encodes functions for phage integration/excision and lysogenic control. DNA encoding functions for phage replication, virion formation and host lysis has been deleted. cI$_{857}$S$_7$ contains a mutant allele of the cI gene which renders the lysogenic control temperature-sensitive, and that aspect of cI$_{857}$S$_7$ is included in the vector. The vector also includes a structural gene for a protein whose controlled synthesis is desired.

Virtually any gene of interest can be cloned into the unique restriction site (XhoI in FIG. 11), and integrated in a host chromosome.

Construction of the Vector

Figure 1:
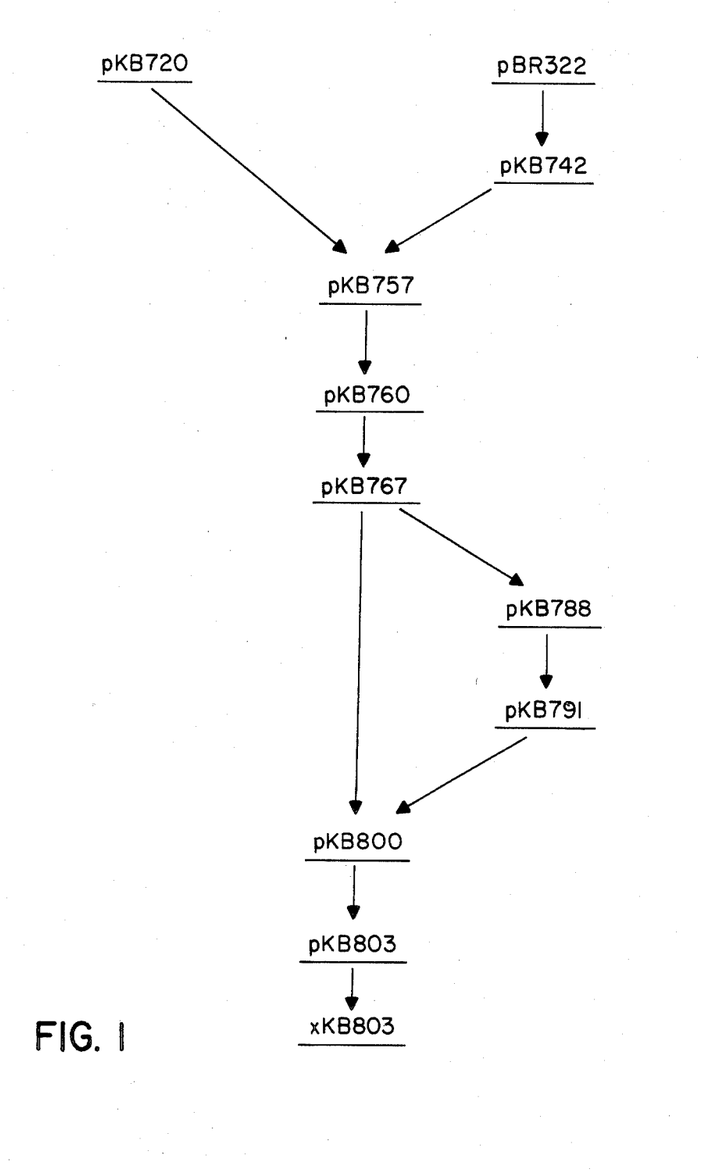
FIG. 1 is a flow chart of the synthesis of the vector xKB803.

The vector is constructed by the steps represented in FIG. 1.

Figure 2:
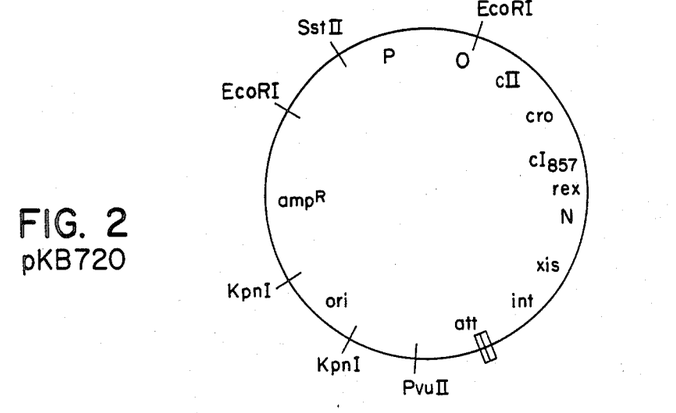
FIGS. 2-10 represent intermediate steps in the construction of the vector of the invention.
Figure 3:
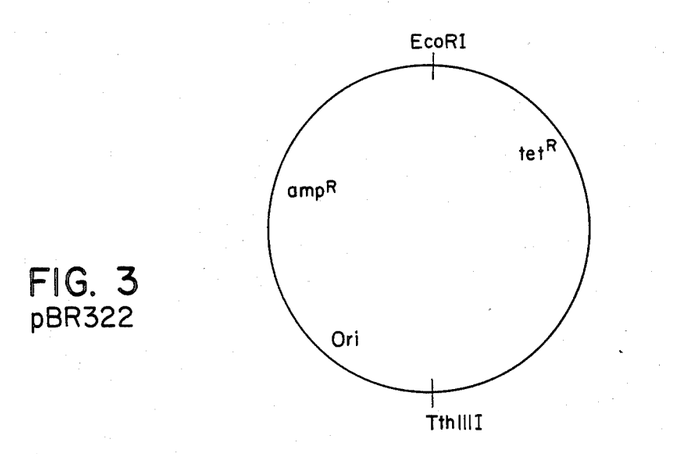
Figure 4:
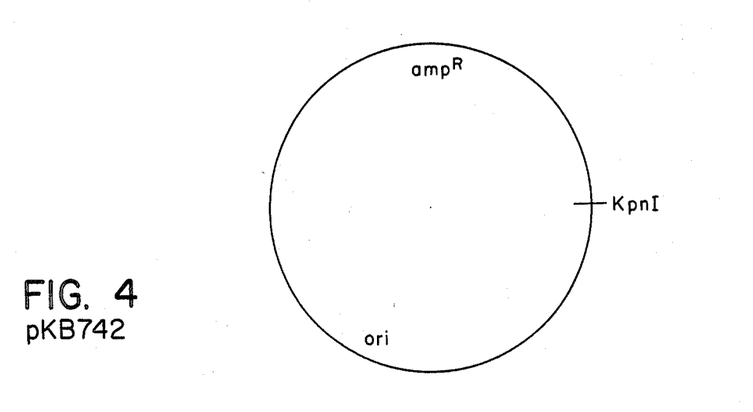
Figure 5:
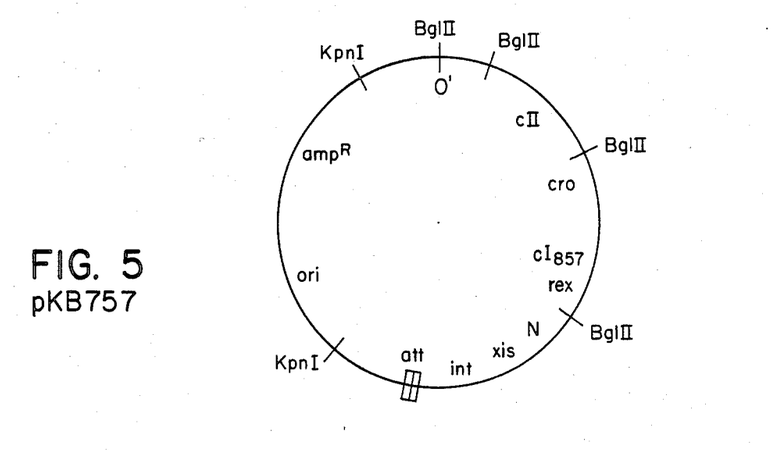

The appropriate cI$_{857}$S$_7$ DNA fragment can be obtained by digesting pKB720 (FIG. 2) or eKB101 (ATCC 39855) [both of which are described in U.S. Ser. No. 655,361, filed Sep. 27, 1984,] with EcoRI and PvuII. The ends of the fragment are converted into KpnI sites by using linkers, and cloned into the KpnI site of pKB742 (FIG. 4) yielding pKB757 (FIG. 5). pKB742 is derived from pBR322 (FIG. 3) by removing the DNA coding for tetracycline resistance between EcoRI and TthIIII and replacing it with a KpnI linker.

pKB757 is treated with BglII to remove the genes cro, O, and cII, in whole or in part for the reasons described below.

The cro gene product binds to the same sites as the cI repressor and regulates gene expression. Principally, it inhibits transcription originating at prm, inhibiting cI transcription. The cro gene product can reduce transcription originating at P$_L$ and thereby interfere with the expression of genes (Xis and Int) necessary for the excision of the element.

The O gene product is required for replication of λ DNA, and should be removed to prevent autonomous replication of the vector.

cII acts as an activator of transcription at the promoters of the cI and int genes. Since cII lies between cro and O, it is removed on the fragment also. Removal of cII is also desirable in order to prevent reintegration of an excised element by cII-dependent expression of int.

Figure 6:
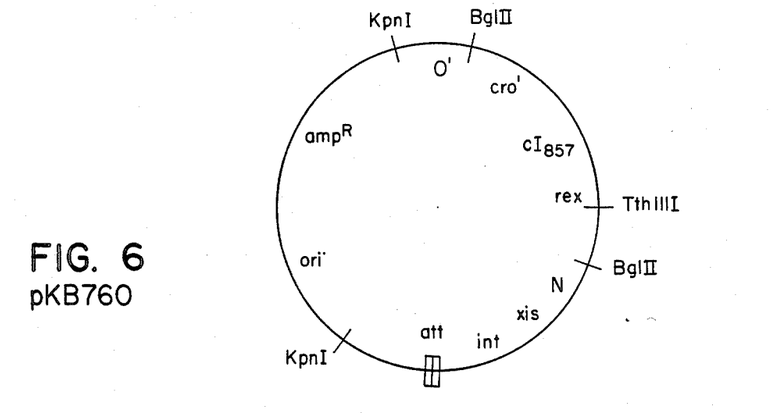
Figure 7:
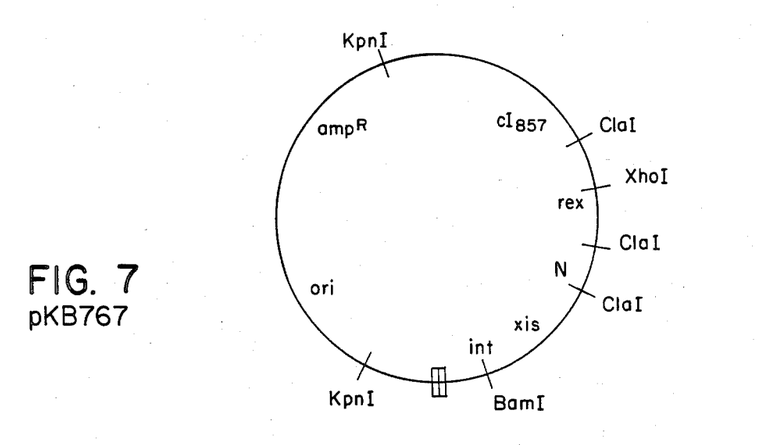

The two largest fragments from the BglII digest of pKB757 are rejoined to yield pKB760 (FIG. 6). Conversion of a unique TthIIII site to a XhoI site by means of a linker results in pKB767 (FIG. 7).

Figure 8:
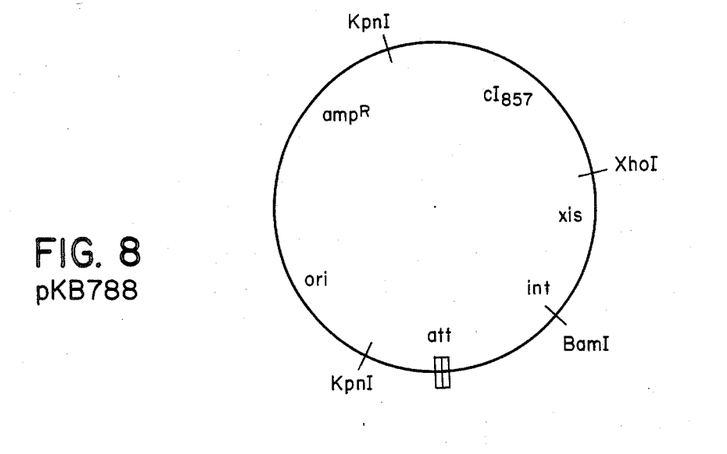
Figure 9:
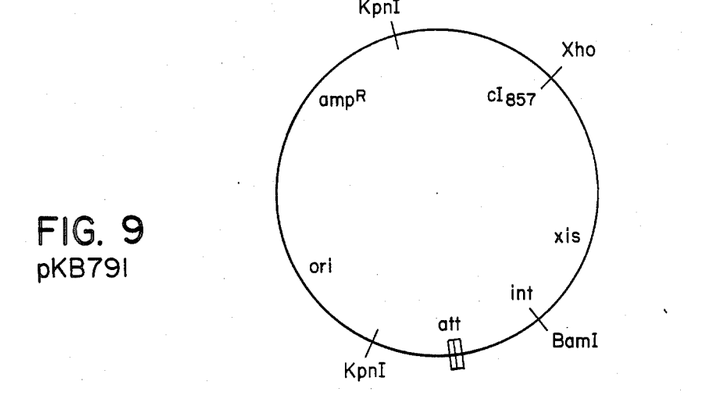

It has been found that the rex gene product can precipitate the lysis of the host bacterium under certain conditions. The rex gene, therefore, is removed by replacing the material between the ClaI sites with a XhoI linker. yielding pKB788 (FIG. 8). Further digestion with XhoI and Bal31, and the addition of a XhoI linker yields pKB791 (FIG. 9), in which the XhoI site is located just outside the cI$_{857}$ gene.

Figure 10:
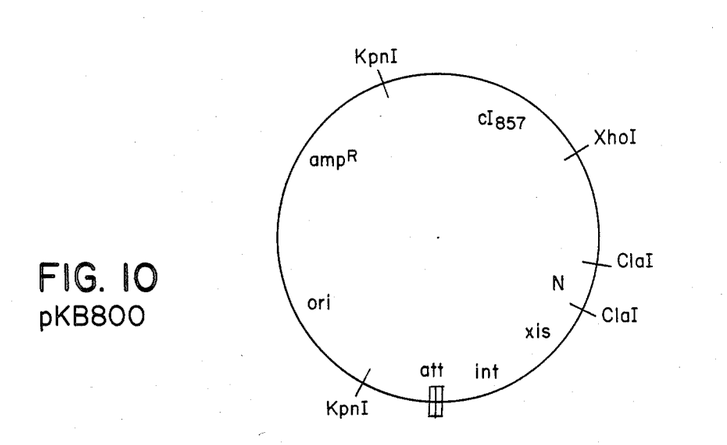
Figure 11:
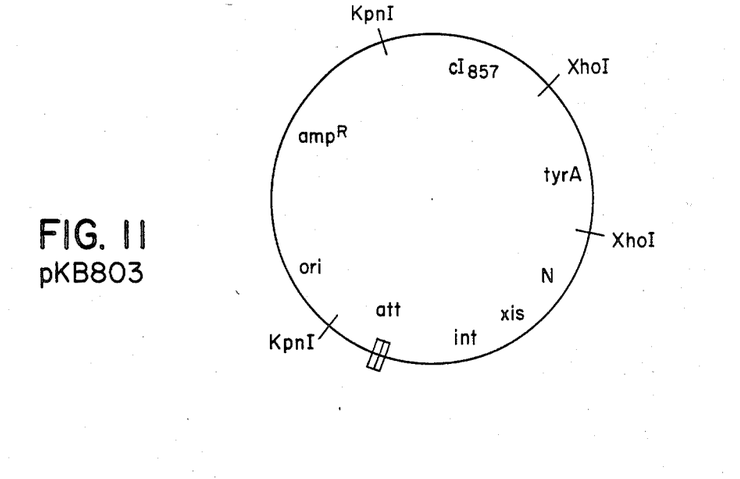
FIG. 11 is a diagram of the vector pKB803
Figure 12:
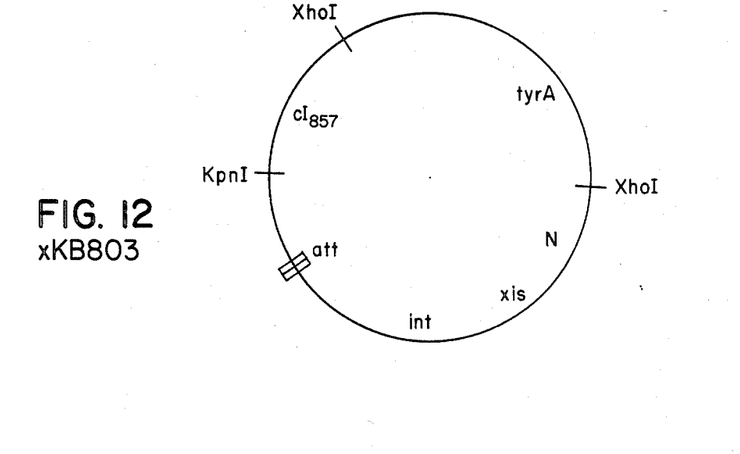
FIG. 12 is a diagram of the excision vector xKB803

The leftward operon containing the genes N, xis, and int is reconstructed on pKB791 by removing the small fragment between the XhoI and BamI sites and replacing it with the XhoI/BamI small fragment of pKB767, yielding pKB800 (FIG. 10). Into the XhoI site of pKB800 is cloned a DNA fragment containing the E. coli tyrA gene, yielding pKB803 (FIG. 11). Digestion of pKB803 with KpnI removes the gene for ampicillin resistance (which can be scored for) and the plasmid replication functions. This yields xKB803.

Vectors pKB800 and pKB803 have been deposited with the American Type Culture Collection under the ATCC accession numbers 53019, and 53020. Applicant's assignee, BioTechnica International, Inc. acknowledges its responsibility to replace these cultures should they die before the end of the term of a patent issued hereon, and its responsibility to notify the ATCC of the issuance of such a patent, at which time the deposits will be made available to the public. Until that time the deposits will be made available to the Commissioner of Patents under the terms of 37 CFR §114 and 35 USC §112.

Use xKB803 is recircularized and transformed into an *E. coli* strain which is auxotrophic for tyrosine, preferably due to a deletion of the tyrA gene and most preferably due to a deletion of the pheA-tyrA-aroF region of its genome to ensure no homology with the tyrA gene to be transferred from the excision vector. One skilled in the art will be able to isolate an *E. coli* mutant that is deleted for the above-described operon by standard techniques. Having done so, the mutant is transformed with xKB803 and vector integrants, defined as KB224::xKB803, are scored on the basis of tyrosine prototrophy.

Integration of the excision vector can be improved to some extent when the transformed cells are co-infected with an integration-deficient helper phage at a multiplicity of infection of 5-10. This improvement may occur because the excision vector xKB803 cannot express its int gene sufficiently due to its low copy number and its lack of a cII activator gene. The diminished ability of the excision vector to autocatalyze its integration in the host chromosome may actually enhance its rate of loss subsequent to temperature shift; once excised, the vector will not reintegrate.

Figure 13:
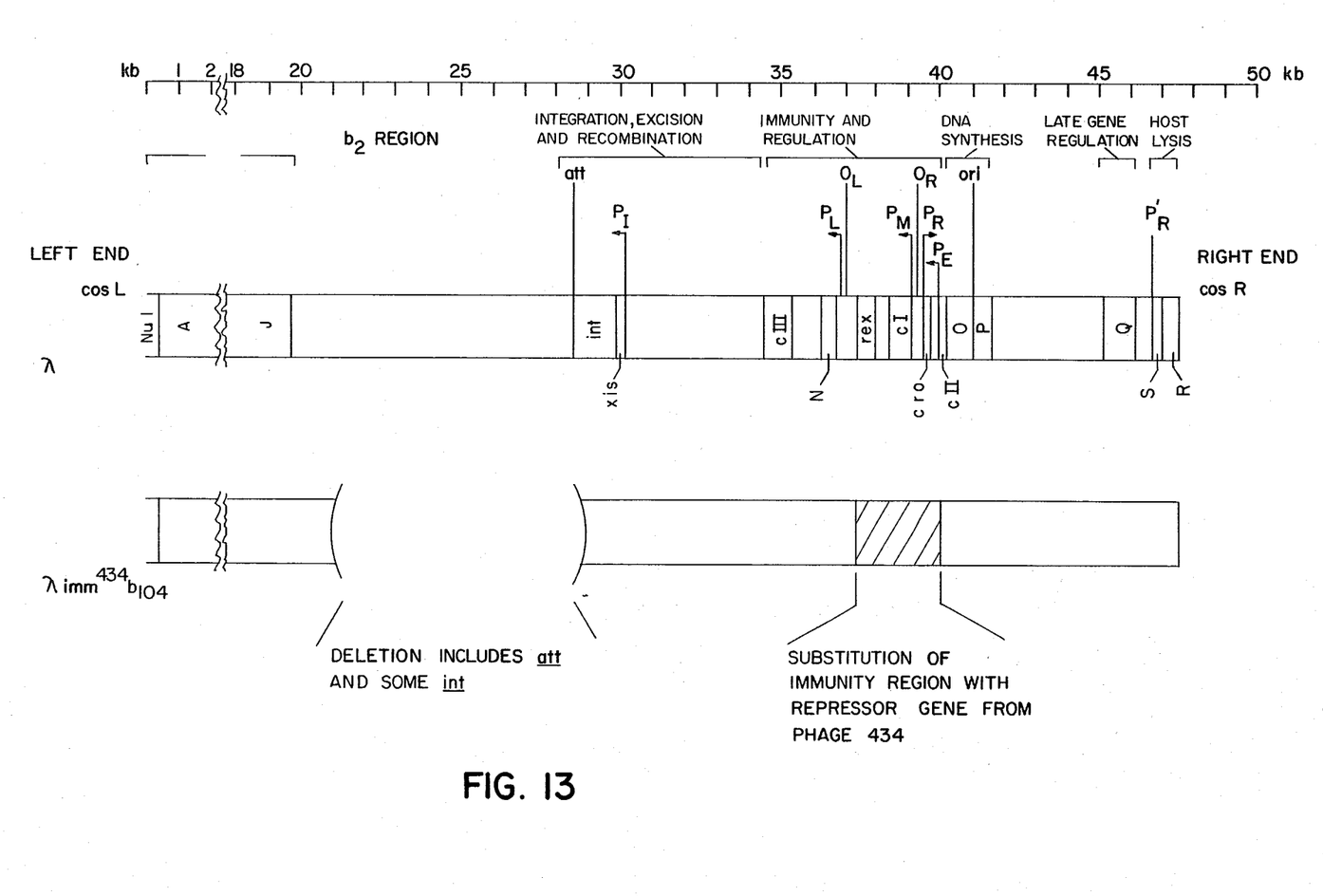
FIG. 13 is a diagram of the integration-deficient helper phage, λimm434b104.

One suitable helper phage is λimm434b104 shown in FIG. 13. Many other helper phages are suitable in that they are not subject to repression by cI encoded on the excision vector and are integration-deficient, but can express the cII and/or int genes sufficiently to improve integration of the excision vector. Other integration deficient phages and their preparation are described in the following: Parkinson et al. (1971) J. Molec. Biol. 56:369; Parkinson (1971) J. Molec. Biol. 56:385; and Davis et al. (1971) J. Molec. Biol. 56:403. Suitable heteroimmune derivatives of these phages are easily prepared by one skilled in the art.

Helper-phage-assisted integrants are selected at 30° C. as tyrA+, bacteria which are immune to lambda infection, sensitive to λimm434b104 (showing that they do not harbor helper phage), and sensitive to ampicillin (showing that they have not acquired all of pKB803). Integrants prepared without the use of a helper-phage are similarly recognized, but without reference to the absence of helper-phage.

Derivatives of *E. coli* which carry the stably integrated excision vector, preferably KB224::xKB803, prepared as described above, can be grown in culture without supplemental tyrosine; however, the cells in such a culture can be expediently converted to tyrosine auxotrophs when the desired cell population has been achieved and enhanced production of product is desired. As long as the culture is grown at 30° C., the temperature-sensitive repressor coded by the $cI_{857}$ gene maintains the vector in a lysogenic state, and the cells retain the excision vector containing the tyrA gene. Upon shifting the culture to 42° C., the $cI_{857}$ repressor is inactivated and derepression of lambda excision functions occurs. The int and xis genes carried on the excision vector are expressed, and the element excises from the chromosome, taking with it the tyrA gene. Because the vector has no origin of replication, it is lost from the cells within a few generations; the cells become tyrA−, and they starve for tyrosine and cease growing. The point at which growth stops is later than, but correlated with, the time at which the temperature shift to 42° C. occurs. The cessation of growth can be reversed by the addition of exogenous tyrosine.

Figure 14:
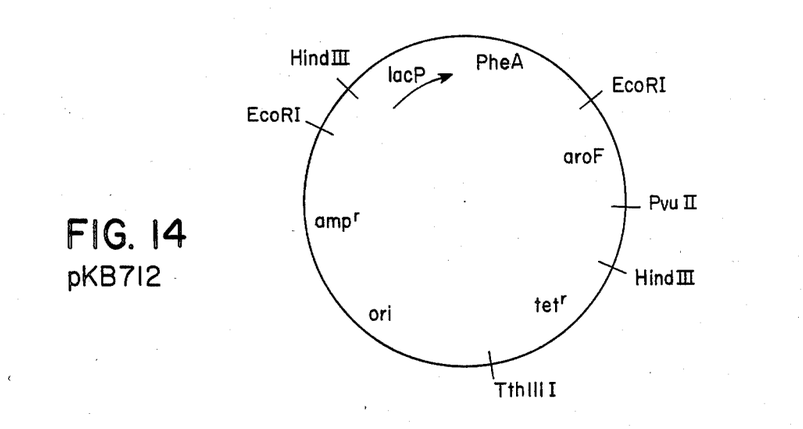
FIG. 14 is a diagram of the plasmid pKB712
Figure 15:
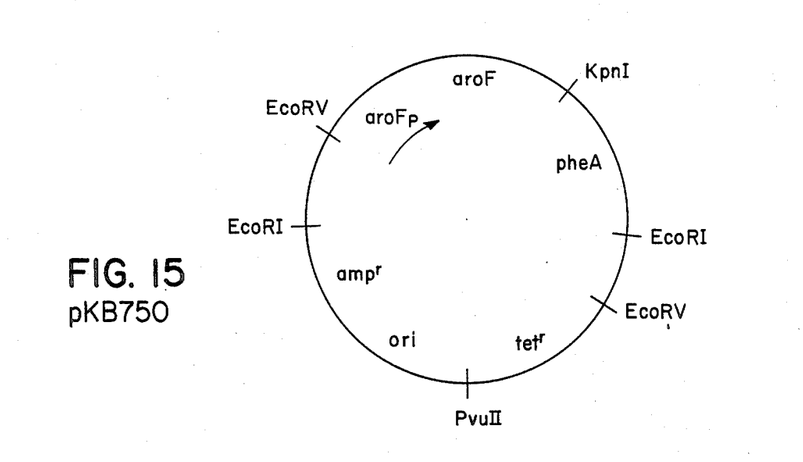
FIG. 15 is a diagram of the plasmid pKB750
Figure 16:
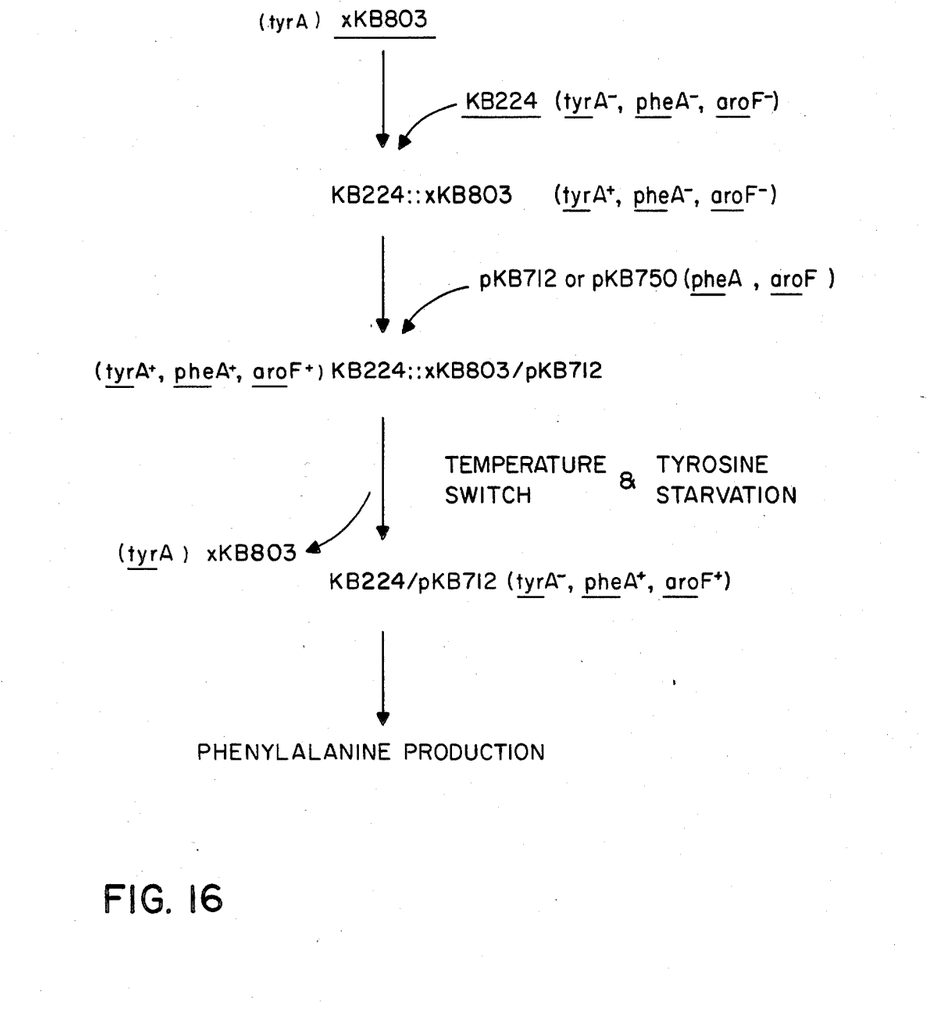
FIG. 16 is a flow chart of phenylalanine production.

The production of phenylalanine using the vector of the invention is outlined in the flow chart in FIG. 16. Derivatives of *E. coli* which carry the stably integrated excision vector, preferably KB224::xKB803, prepared as described above, are tyrA+, pheA−, aroF−. The requisite genes for the production of phenylalanine, pheA and aroF, are provided by transforming KB224::xKB803 with a plasmid containing these elements, for example, pKB712, ATCC No. 39856 (FIG. 14) or pKB750. ATCC No. 39857 (FIG. 15) (see Backman, U.S. Ser. No. 653,193 filed Sept. 24, 1984. The transformed bacteria, KB224::xKB803/pKB712 or KB224::xKB803/pKB750, are now tyrA+, pheA+, aroF+. The culture is maintained at the permissive temperature for log phase growth until the cell population has reached the desired density. Upon shifting the temperature to 42° C., the vector element containing the tyrA gene is excised from the bacterial chromosome and eventually lost from the cells. By eliminating an enzyme which diverts precursor metabolites from the phenylalanine biosynthesis pathway and "turning on" the preceeding steps in the pathway via tyrosine starvation, phenylalanine synthesis proceeds at an enhanced rate.

OTHER EMBODIMENTS

Other embodiments are within the following claims. For phenylalanine production, excision vectors containing tyrR and/or trpE could also be used. For example, where different genetic complements are desirable at different times, this versatile method of externally controlled change from one genetic complement to another can be applied to other gene systems including multiple gene systems. Other cell-growth related genes can be used to control cell growth in a fermentation process. For example, hosts that are defective in expressing the gene encoding phosphoenolpyruvate carboxylase (ppc) such as KB280 (ATCC 33927) are described in U.S. Ser. No. 539,981, filed Oct. 7, 1983. The excision vector of the invention can be used to insert an effective ppc gene for growth and then to excise it.

For producing threonine, genes relating to isoleucine biosynthesis are useful for cell growth and hinder product production.

For tryptophan production, the following genes are useful for cell growth and hinder product production: tna (tryptophanase), trpR, aroP, tyrA, and pheA.

For proline production, a gene coding for proline oxidase can be included on the excision vector.

The above-mentioned genes can be cloned by standard techniques, e.g. from *E. coli*.

We claim:

1. An *Escherichia coli* bacterial cell which undergoes controllable excision of a genetically engineered, chromosomally located DNA segment, wherein said cell comprises:

DNA encoding lambdoid int and xis genes, operably positioned to be transcribed under the control of an external stimulus, wherein said external stimulus causes excision of a chromosomally located DNA segment, and a gene function is lost thereby from said cell and wherein said chromosomally located DNA segment, when excised, is incapable of replication, and wherein said DNA segment comprises a pair of lambdoid phage att sites, positioned at opposite ends thereof and a gene determining a function in said cell, and wherein said function is lost in the absence of said chromosomally located DNA segment.

2. The *E. coli* cell of claim 1 wherein said genetically engineered, chromosomally located DNA segment lacks sufficient homology to integrate into said chromosome in the absence of expression of a lambdoid phage int gene.

3. The *E. coli* cell of claim 1 wherein said DNA encoding int and xis genes are operably positioned for transcription under the control of lambdoid phage cI gene product.

4. The *E. coli* cell of claim 1 wherein said DNA encoding int and xis genes are operably positioned on said chromosomally located DNA segment to be excised.

5. The *E. coli* cell of claim 1 wherein said cell further comprises a helper phage comprising a lambdoid phage int gene, and wherein said helper phage effects integration of said chromosomally located DNA segment into the chromosome of said cell prior to the controlled excision of said segment and subsequent loss of said segment from said cell.

6. The *E. coli* cell of claim 1 wherein said gene function is part of an aromatic amino acid synthesis pathway.

7. The *E. coli* cell of claim 6, wherein said gene is tyrA, tyrR, or trpE.

8. The *E. coli* cell of claim 6, wherein said gene is trpR, aroP, tyrA, or pheA.

9. The *E. coli* cell of claim 1, wherein said gene codes for an enzyme in the isoleucine biosynthesis pathway.

10. The *E. coli* cell of claim 1, wherein said gene codes for proline oxidase.

11. The *E. coli* cell of claim 1, wherein said gene is ppc.

12. The *E. coli* cell of claim 1, wherein said chromosomally located DNA segment comprises DNA from a plasmid that has been integrated in said cell, wherein said plasmid is: a derivative of pKB800, deposited as ATCC 53019, wherein ori has been deleted and into which derivative said gene has been inserted; or a derivative of pKB803, deposited as ATCC 53020, from which ori has been deleted.

13. A method of producing a desired compound comprising:
   culturing the *E. coli* cells of claim 1 to a desired population density;
   controlling said external stimulus that causes excision of said gene from the chromosomes of members of said *E. coli* cell population;
   culturing cells in a medium wherein said cells have said gene excised from their chromosomes;
   recovering said compound produced thereby.

14. The method of claim 13 wherein said gene codes for a function and said medium lacks components required to permit growth in the absence of said function.

15. The method of claim 13 or claim 14 wherein said *E. coli* cells produce said desired compound via a synthesis pathway comprising intermediate compounds, and wherein said gene codes for an enzyme that converts an intermediate of said pathway to a compound outside said synthesis pathway.

16. The method of claim 13 wherein said *E. coli* cells produce said desired compound via a synthesis pathway comprising intermediate compounds, wherein said gene codes for a function regulating expression of an enzyme, and wherein one of said intermediate compounds is a substrate for said enzyme.

17. The method of claim 15, wherein said desired compound is phenylalanine and wherein said gene codes for an enzyme that catalyzes a step in the synthesis of tyrosine or tryptophan.

18. The method of claim 13, wherein said desired compound is phenylalanine, and wherein said gene is selected from the group consisting of tyrA, tyrR and trpE.

19. The method of claim 13, wherein said desired compound is tryptophan and said gene is selected from the group consisting of tna, trR, aroP, tyrA, or pheA.

20. The method of claim 14, wherein said compound is threonine and wherein said gene codes for an enzyme in the isoleucine biosynthesis pathway.

21. The method of claim 14, wherein said compound is proline and wherein said gene codes for proline oxidase.

22. The method of claim 13, wherein said gene is ppc.

23. A method of making the *E. coli* cell of claim 1, wherein the loss of expresssion of said gene is controlled, said method comprising:
   (a) transforming a host cell with an engineered plasmid, wherein said plasmid comprises a DNA segment that lacks the ability to extrachromosomally replicate in said cell, and wherein said DNA segment comprises said gene and a lambdoid phage att site;
   (b) allowing integration and expression of said gene in said *E. coli* cell; and then
   (c) effecting the excision of said chromosomal DNA segment by said extenal stimulus.

24. An engineered plasmid that lacks the ability to replicate in *E. coli* wherein said plasmid comprises: a lambdoid att site; a gene encoding a function whose expression is to be controlled; and int and xis genes from a lambdoid phage, wherein said int and xis genes are operably positioned and oriented for expression under the control of a lambdoid cI gene.

25. The plasmid of claim 24 wherein said plasmid is: a derivative of pKB800 ATCC 53019 wherein ori has been deleted and into which said gene has been inserted or a derivative of pKB803 ATCC 53020 wherein ori has been deleted.

26. The plasmid of claim 24 wherein said gene is tyrA, tyrR, or trpE.

27. The plasmid of claim 24, wherein gene is trpR, aroP, tyrA, or pheA.

28. The plasmid of claim 24, wherein said gene codes for an enzyme in the isoleucine biosynthesis pathway.

29. The plasmid of claim 24, wherein said gene codes for proline oxidase.

30. The plasmid of claim 24, wherein said gene is ppc.

* * * * *